(12) United States Patent
Dessort et al.

(10) Patent No.: US 8,518,706 B2
(45) Date of Patent: Aug. 27, 2013

(54) HYDROGEN SULPHIDE SAMPLING METHOD

(75) Inventors: Daniel Dessort, Pau (FR); Robert Le Van Loï, Pau (FR); Nadine Loubere, Pardies (FR)

(73) Assignee: Total S.A., Courbevoie (FR)

( * ) Notice: Subject to any disclaimer, the term of this patent is extended or adjusted under 35 U.S.C. 154(b) by 98 days.

(21) Appl. No.: 12/988,771

(22) PCT Filed: Apr. 20, 2009

(86) PCT No.: PCT/IB2009/005289
§ 371 (c)(1),
(2), (4) Date: Oct. 20, 2010

(87) PCT Pub. No.: WO2009/130559
PCT Pub. Date: Oct. 29, 2009

(65) Prior Publication Data
US 2011/0033943 A1 Feb. 10, 2011

(30) Foreign Application Priority Data

Apr. 22, 2008 (FR) ...................... 08 02241

(51) Int. Cl.
*G01N 33/00* (2006.01)
*G01N 21/25* (2006.01)
*B01D 59/44* (2006.01)

(52) U.S. Cl.
USPC ........... 436/121; 422/400; 422/401; 422/402; 422/405; 422/416; 422/430; 436/119; 436/120; 436/167

(58) Field of Classification Search
USPC . 422/400–402, 405, 416, 430; 436/119–121, 436/167–168
See application file for complete search history.

(56) References Cited

U.S. PATENT DOCUMENTS

| | | | | |
|---|---|---|---|---|
| 1,512,893 | A * | 10/1924 | Fulweiler | 436/121 |
| 2,174,349 | A * | 9/1939 | Littlefield | 436/121 |
| 2,232,622 | A * | 2/1941 | Moses et al. | 422/87 |
| 2,895,807 | A * | 7/1959 | Sorg et al. | 422/91 |
| 3,208,828 | A * | 9/1965 | O'Neal, Jr. et al. | 436/120 |

(Continued)

FOREIGN PATENT DOCUMENTS

| | | |
|---|---|---|
| FR | 2113612 A | 6/1972 |
| FR | 2462702 A1 | 2/1981 |

(Continued)

OTHER PUBLICATIONS

Quitmann, E., Zeitschrift für Analytische Chemie 1937, 109, 16-21.*

(Continued)

*Primary Examiner* — Arlen Soderquist
(74) *Attorney, Agent, or Firm* — Marsh Fischmann & Breyfogle LLP

(57) ABSTRACT

The invention relates to a method for sampling a sulphur-containing solid product including supplying a gas flow comprising hydrogen sulphide, bringing the gas flow into contact with a solid reagent and reacting the solid reagent with the hydrogen sulphide contained in the gas flow, the reaction fixing the sulphur of the hydrogen sulphide by forming a sulphur-containing solid product which is different in color from the solid reagent, and recovering the sulphur-containing solid product. The invention also relates to a device suitable for the implementation of this method.

6 Claims, 2 Drawing Sheets

(56) References Cited

U.S. PATENT DOCUMENTS

| | | | | |
|---|---|---|---|---|
| 3,847,552 A | * | 11/1974 | Hobgood et al. | 436/28 |
| 4,174,202 A | * | 11/1979 | Simpson | 436/121 |
| 4,258,000 A | | 3/1981 | Obermayer | |
| 4,348,358 A | * | 9/1982 | McKee et al. | 422/416 |
| 4,478,792 A | * | 10/1984 | McConnaughey et al. | 422/401 |
| 4,977,093 A | * | 12/1990 | Cooke | 436/119 |
| 5,120,511 A | * | 6/1992 | Luft | 422/86 |
| 5,529,841 A | * | 6/1996 | Neihof | 428/328 |
| 6,133,041 A | * | 10/2000 | Park | 436/121 |
| 6,319,722 B1 | * | 11/2001 | Litwin et al. | 436/121 |
| 6,322,750 B1 | * | 11/2001 | Barclay | 422/424 |
| 6,939,711 B2 | * | 9/2005 | Goff et al. | 435/419 |
| 2001/0051376 A1 | | 12/2001 | Jonker | |
| 2003/0134426 A1 | * | 7/2003 | Jiang et al. | 436/121 |
| 2010/0059375 A1 | * | 3/2010 | Weiller et al. | 204/433 |

FOREIGN PATENT DOCUMENTS

| | | |
|---|---|---|
| GB | 1392720 A | 4/1975 |
| GB | 2344365 A | 6/2000 |
| WO | 2005029003 A2 | 3/2005 |

OTHER PUBLICATIONS

Jacobs, M. B. et al, Analytical Chemistry 1957, 29, 1349-1351.*
Hobbs, A. P., Analytical Chemistry 1962, 34, 91R-98R.*
Gilardi, E. F. et al, Journal of the Air Pollution Control Association 1963, 13, 305-311.*
Wohlers, H. C. et al, Journal of the Air Pollution Control Association 1966, 16, 19-21.*
Volkan, M. et al, Talanta 1998, 47, 585-593.*
Bagon, D. A. et al, Annals of Occupational Hygiene 1973, 16, 133-139.*

* cited by examiner

HYDROGEN SULPHIDE SAMPLING METHOD

FIELD OF THE INVENTION

The present invention relates to a method for sampling hydrogen sulphide ($H_2S$), as well as a device suitable for the implementation of this method.

TECHNICAL BACKGROUND

The management of hydrogen sulphide ($H_2S$) plays a major part in the field of gas and oil production. In fact, hydrogen sulphide, which can be present in a molar concentration that can vary greatly depending on the deposits (from a few ppm to several tens of %), is a gas which is not only extremely toxic (fatal at a low concentration) but also corrosive in the presence of water. It is therefore important to treat it, as well as to adopt installations adapted to its presence.

The concentration of hydrogen sulphide can increase dramatically, or even appear, during production, requiring complex and costly adaptations of the production methods. Such an increase or appearance can have several sources, some natural and others artificial.

Thus, examples of possible sources of hydrogen sulphide are:

- thermal reduction of sulphates by the hydrocarbons at a high temperature;
- bacterial reduction of sulphates;
- in the case of injection of hydrochloric acid into the rock during production, reaction of the former with pyrite;
- contamination of the considered reservoir of hydrocarbons by a second reservoir of hydrocarbons having a higher $H_2S$ content.

It is important to identify the sources of the hydrogen sulphide for each deposit, in order:

- to reduce when possible the hydrogen sulphide content (for example by means of a bactericidal treatment or by interrupting the injection of hydrochloric acid depending on the case); or
- to predict the evolution over time of the $H_2S$ content, in order to dimension the installations accordingly, preferably to within one-tenth of percent of hydrogen sulphide.

This identification of the sources of hydrogen sulphide is difficult; in the first place it is based on the isotopic measurement of the sulphur present in the hydrogen sulphide. In fact, depending on the chemical or biochemical processes at the origin of the formation of the hydrogen sulphide, the isotopic fractionation (i.e. the proportion of heavy isotope $^{34}S$ involved in the various conversion processes) varies. A measurement of the ratio of molar concentration of the heavy isotope $^{34}S$ to the majority isotope $^{32}S$ (isotopic ratio) therefore provides direct information on the origin of the hydrogen sulphide, which is a valuable item of information for production strategies.

In order to carry out the measurement of the isotopic ratio of the sulphur, it is usual to oxidize the hydrogen sulphide beforehand. The oxidation-reduction reaction is brought about by bubbling the gas containing the hydrogen sulphide through a solution containing cadmium acetate. The cadmium acetate reacts with the hydrogen sulphide to form cadmium sulphide. The actual isotopic ratio measurement is carried out on the sulphur present in the cadmium sulphide thus obtained.

The measurement of the isotopic ratio of the sulphur is carried out by mass spectrometry. This measurement therefore requires heavy laboratory equipment; it cannot be carried out directly on the site.

Two pre-analysis sampling methods are currently used. These involve:

- taking a sample of gas containing hydrogen sulphide on site in a pressurized bottle, and sending the pressurized bottle to the laboratory where the isotopic analysis will take place (the intermediate reaction with the cadmium acetate solution therefore takes place in the laboratory); or
- taking a sample of gas containing hydrogen sulphide, carrying out the reaction of hydrogen sulphide with the aqueous solution of cadmium acetate on site, and sending the solution obtained to the laboratory where the isotopic analysis will take place.

However, these two methods pose considerable problems.

With the first method, the filling of a pressurized bottle is an expensive operation, time-consuming and not very practical to implement under site conditions. Furthermore, $H_2S$ is a gas which is toxic for humans, and the transport, generally by air, of samples of compressed gas containing $H_2S$ can be a very prolonged operation.

Finally, the quantity of $H_2S$ present in the pressurized bottle may not be sufficient to carry out the isotopic measurement.

The second method involves carrying out the oxidation-reduction reaction between the hydrogen sulphide and the cadmium acetate directly on site, and sending an aqueous solution containing a cadmium sulphide precipitate to the analysis laboratory. Whilst this solution is satisfactory in terms of transport, it is difficult to implement. In fact, carrying out oxidation-reduction reactions on site requires fragile laboratory equipment, not very compatible with the site, and personnel qualified to use it. Obtaining reliable and reproducible analysis results requires strict observance of the operating procedure, which is not always possible under site conditions.

Furthermore, for reasons of on-site safety, it is preferable to minimize handling operations under site conditions.

Moreover, the application GB 2344365 describes a device suitable for sampling a determined quantity of fluid of hydrocarbons in situ in a reservoir. A component of the device comprises a material capable of reacting with hydrogen sulphide. The material can be for example a metal, a metal oxide, or an organic compound. However, the system described is mainly intended for measuring the concentration of hydrogen sulphide directly in the fluid of the deposit. It is moreover extremely heavy, complex and expensive to implement due to the difficulty of taking a sample in situ.

Thus, there is a real need to develop a system allowing the isotopic measurement of the hydrogen sulphide which is robust, simple to use under operating site conditions, safe and inexpensive.

SUMMARY OF THE INVENTION

The invention relates firstly to a method for sampling a sulphur-containing solid product comprising:

- supplying a gas flow comprising hydrogen sulphide;
- bringing the gas flow into contact with a solid reagent and reacting the solid reagent with the hydrogen sulphide contained in the gas flow, said reaction fixing the sulphur of the hydrogen sulphide by forming a sulphur-containing solid product which is different in colour from the solid reagent; and recovering the sulphur-containing solid product.

According to an embodiment, the solid reagent is constituted by cadmium acetate crystals.

According to an embodiment, the gas flow originates from a deposit of hydrocarbons.

According to an embodiment, the stage of bringing into contact is carried out continuously and the gas flow is evacuated after having been brought into contact with the solid reagent.

According to an embodiment, the pressure in the contact chamber during the stage of bringing into contact is comprised between 0 and 10 effective bar, preferably between 0 and 5 effective bar.

According to an embodiment, said method also comprises the following stages:
- transport of the sulphur-containing solid product to an installation for the isotopic measurement of the sulphur;
- isotopic measurement of the sulphur in the sulphur-containing solid product within the installation for the isotopic measurement of the sulphur.

A subject of the invention is also a device for sampling a sulphur-containing solid product comprising:
- a contact chamber, comprising a solid reagent, said solid reagent being capable of reacting with hydrogen sulphide and the reaction of the solid reagent with hydrogen sulphide producing a change in colouration and fixing the sulphur of the hydrogen sulphide by forming a sulphur-containing solid product;
- gas flow delivery means, feeding the contact chamber inlet;
- gas flow evacuation means, connected to the contact chamber outlet; and
- means of displaying the change in colouration of the solid reagent in the detachable contact chamber.

According to an embodiment, the contact chamber is detachable.

According to an embodiment, the means of displaying the change in colouration of the solid reagent consist in the contact chamber having a translucent or transparent wall, preferably made of plastic.

According to an embodiment, the contact chamber comprises two filters, upstream and downstream of the solid reagent.

According to an embodiment, the solid reagent is constituted by cadmium acetate crystals.

According to an embodiment, said device comprises one or more of the following components upstream of the contact chamber:
- a pressure reducer;
- a flow-control valve;
- a purge system;
- and optionally a flow meter downstream of the contact chamber.

According to an embodiment, the contact chamber is provided with means for breaking a wall of the contact chamber.

According to an embodiment, the method according to the invention is implemented by means of the device according to the invention.

A subject of the invention is also a contact chamber comprising a solid reagent, said solid reagent being capable of reacting with hydrogen sulphide and the reaction of the solid reagent with hydrogen sulphide producing a change in colouration and fixing the sulphur of the hydrogen sulphide by forming a sulphur-containing solid product, said contact chamber having a translucent or transparent wall, preferably made of plastic.

The present invention makes it possible to overcome the drawbacks of the state of the art. It provides more particularly a method for sampling hydrogen sulphide (and an associated device) allowing the isotopic measurement of the sulphur which is at the same time robust, easy to use under production site conditions, safe and inexpensive.

This is achieved thanks to the use of a solid reagent capable of reacting with the hydrogen sulphide and fixing the sulphur present in the latter, by forming a sulphur-containing solid product, the reaction being accompanied by a change in colouration.

The invention offers more particularly at least one of the advantageous characteristic features listed below, or even two or more.

- The use of a solid reagent makes it possible to avoid the problems of transport and handling safety which are encountered with liquid products or with compressed gas. In particular, the sulphur-containing solid product is advantageously less toxic and less corrosive than hydrogen sulphide,
- The total period separating the sampling of a gas flow comprising hydrogen sulphide and the isotopic measurement of the sulphur is reduced. The frequency of the sampling and of the isotopic measurement can thus be considerably increased.
- The method according to the invention (and the associated device) is easy to implement on a hydrocarbon production site, without requiring the presence of a specialist technician.
- Preferably, the device has no glass components, so that normal safety measures are sufficient for its use.
- The isotopic measurement of the sulphur allowed by the invention is at least as reliable as an isotopic measurement carried out by conventional methods.
- The samples of sulphur-containing solid product can be kept for a long time.
- The change in colouration associated with the reaction makes it possible on the one hand to verify the presence of hydrogen sulphide, and on the other hand to adjust the period for which the solid reagent is brought into contact with the gas flow during the time strictly necessary for fixing a maximum quantity of sulphur, without having to know beforehand the order of magnitude of the hydrogen sulphide content of the gas flow.
- The invention can be implemented at a low cost, in particular at a cost hundreds of times lower than that of the method using pressurized bottles.
- The device according to the invention is miniaturized compared with the existing systems, it takes up little space and can easily be transported by hand in a case.
- The sensitivity of the measurements is increased compared with the method using pressurized bottles. In fact, it is sufficient to circulate just as much gas flow as is necessary in the contact chamber in order to obtain a sufficient quantity of sulphur-containing material on which to carry out the isotopic measurement.
- The ease of use of the method makes it possible to carry out numerous analyses, which makes it possible to increase the sampling and in fine the reliability of the measurements.

DESCRIPTION OF EMBODIMENTS OF THE INVENTION

The invention is now described in more detail and in non-limitative manner in the following description.

Device for Sampling $H_2S$

Figure 1:
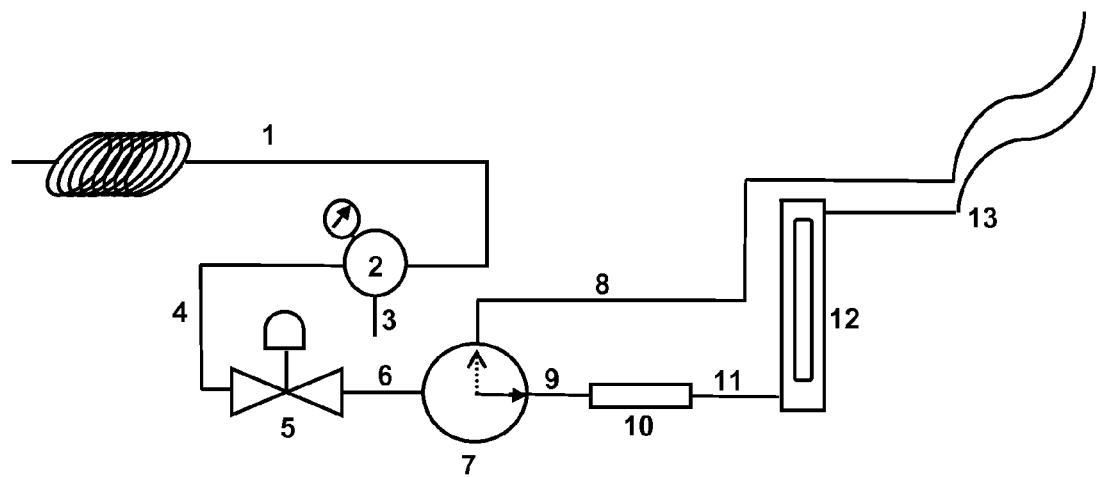
FIG. 1 shows a schematic diagram of an embodiment of the device according to the invention.

With reference to FIG. 1 (and also in relation to the photograph of FIG. 3), according to an embodiment, the sampling device according to the invention comprises a gas flow delivery line 1. This can be for example a stainless steel tube connected to a coil. This gas flow delivery line 1 can be for example connected to a separator or to a wellhead installation, in the context of a use of the device on an oil or gas production site. It is also possible to connect the gas flow delivery line to a supply of inert gas (for example a nitrogen pressurized bottle) or of compressed air in order to aerate the device in order to clean it, in particular between two sampling operations.

The gas flow delivery line 1 feeds a pressure reducer 2, intended to reduce the pressure of the gas flow. The pressure reducer 2 is advantageously provided with a bleed line 3.

A first gas flow transport line 4, which feeds a flow-control valve 5, is connected to the outlet of the pressure reducer 2.

A second gas flow transport line 6, which supplies a two-way valve 7, is connected to the outlet of the flow-control valve 5. This two-way valve 7, according to its actuation, either purges the system via a bleed line 8 (for cleaning the system for example by means of flushing with an inert gas), or supplies a contact chamber 10, via a third gas flow transport line 9.

A fourth gas flow transport line 11, which supplies a flow meter 12, which can be in particular a ball flow meter and which makes it possible to display whether the system is operating normally or whether it is blocked, is connected to the outlet of the contact chamber 10. Gas evacuation means 13 are connected to the outlet from the flow meter 12.

The gas evacuation means 13 can in particular evacuate the gas flow directly into the ambient atmosphere, taking account of the low gas flow rate which is in principle used within the framework of the invention, and taking account of the low hydrogen sulphide content of the gas flow at the outlet, since virtually all of the hydrogen sulphide contained in the gas flow reacts in the contact chamber 10 when the device is operating.

Advantageously, the whole of the device is capable of withstanding a temperature comprised between −30° C. and +50° C., preferably between −40° C. and +60° C., advantageously between −50° C. and +70° C. This proves important given the extreme temperature conditions which can be encountered in the various regions of the world where hydrocarbon deposits are situated.

The device preferably has no glass components. The device preferably has no battery and no electric parts, in order that that the system does not present any detonation risk.

Figure 3:
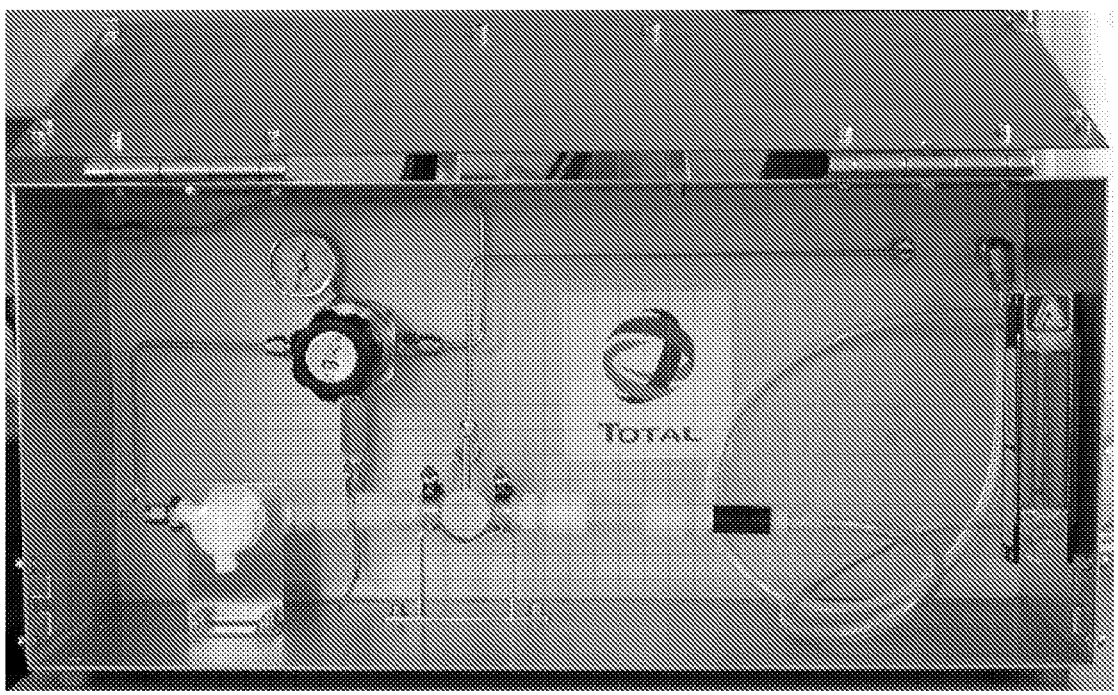
FIG. 3 is a photograph of an example of a device according to the invention.

The whole of the device is preferably provided in an easily transportable carrying case, for example made of stainless steel, (see FIG. 3 in this connection). The maximum dimension of the carrying case (length) can be less than 1 m, preferably less than 80 cm or even less than 60 cm.

Figure 2:
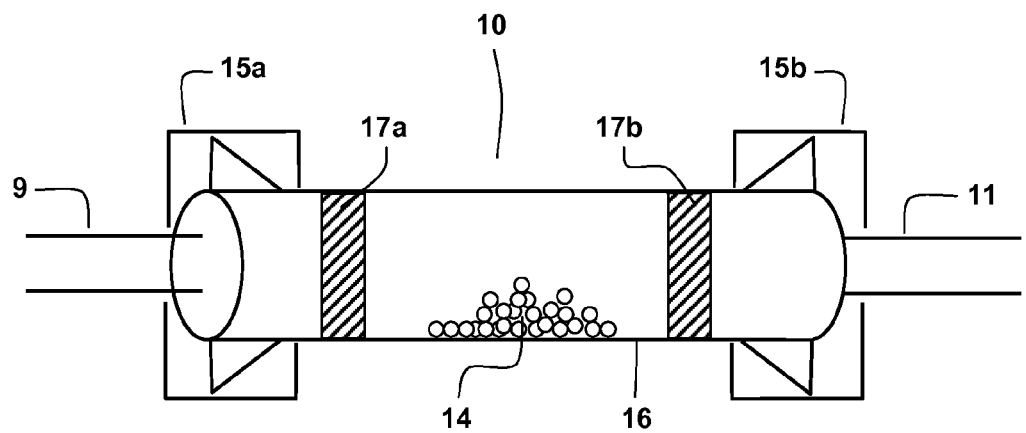
FIG. 2 shows a detailed diagram of an embodiment of the contact chamber used in the device according to the invention.

With reference to FIG. 2, the contact chamber 10 can be cylindrical in shape, preferably from 5 to 15 mm in external diameter and from 7 to 15 cm in length, for example approximately 10 mm in external diameter and 10 cm in length. The thickness of the wall 16 of the contact chamber 10 can be approximately 2 to 5 mm, for example approximately 3 mm. The contact chamber can for example be produced using a Nalgene® tube.

At least part of the wall 16 must be transparent or translucent, so that it is possible to observe the inside of the contact chamber 10. For example, it is possible to provide a window in the wall 16. Alternatively and preferably, the whole of the wall 16 is transparent or translucent. Advantageously, the wall 16 of the contact chamber is made of plastic, for example polycarbonate or polyvinylidene fluoride (Kynar®). Preferably the plastic is unbreakable, i.e. shock-resistant. The wall 16 must be inert vis-à-vis hydrogen sulphide.

Inside the contact chamber 10 two filters 17a, 17b are arranged, which form an obstacle to the passage of particles larger than 100 microns in size while still allowing the passage of the gases. The filters 17a, 17b can for example be made of glass wool or cellulose, with optionally a tubular component made of polypropylene to hold them in place.

The solid reagent 14 is arranged between the filters 17a, 17b.

Connectors 15a and 15b at both ends of the contact chamber 10 provide the connection respectively to the third gas flow transport line 9 and the fourth gas flow transport line 11.

The solid reagent 14 is preferably constituted by crystal grains of a reactive material. Alternatively, the solid reagent 14 can be constituted by a support material (for example beads of silica or another material) coated with reactive material.

The reactive material is chosen such that it is capable of reacting with hydrogen sulphide so as to provide a solid product while still fixing the sulphur of the hydrogen sulphide, and so that the reaction with the hydrogen sulphide is accompanied by a change in colouration (i.e. the solid product has a colouration different from that of the reactive material).

By change in colouration is meant a change in the colour of the material which can be clearly distinguished by a user with the naked eye. For example, the change in colouration can be from white to yellow or orange.

Preferably, the reactive material is not a material the initial colour of which is dark, as this does not make it possible to correctly display the oxidation-reduction reaction with the hydrogen sulphide. The metals and metal oxides are generally dark-coloured materials, the use of which is not preferred. For example iron oxide is a black-coloured metal. In the presence of hydrogen sulphide, it rapidly changes to greenish ferrous oxide then to rust-coloured ferric oxide, which is not considered to be a change in colour clearly distinguished by a user with the naked eye.

The reactive material is therefore preferably a light-coloured (ideally white) solid material, for example cadmium acetate. Cadmium acetate, the crystals of which are white, reacts with hydrogen sulphide to form cadmium sulphide (yellow crystals) and acetic acid.

The quantity of solid reagent in the contact chamber is preferably comprised between 1 mg and 10 g, more particularly between 10 mg and 1 g, in particular between 50 mg and 500 mg.

In the case where the solid reagent is constituted by cadmium acetate crystals, a quantity of crystals of approximately 200 mg is appropriate.

In the device according to the invention, the contact chamber 10 is preferably detachable, i.e. it can be removed from the device, preferably by hand, without the aid of tools, and can be replaced.

In this case, the contact chamber 10 can therefore be considered as a disposable item. Once removed from the device, the contact chamber 10 can be transported, easily opened in order to release the solid product of the reaction and discarded.

As a result, the contact chamber 10 also constitutes a subject of the invention in itself.

Alternatively, the contact chamber 10 can be permanently integrated into the device. In this case, the contact chamber 10 is provided with an opening system, in order to be able to manually extract the solid product of the reaction.

Method for Sampling $H_2S$

The method according to the invention can be implemented using the device described above. In order to do this, the device is supplied with a gas flow containing hydrogen sulphide, in particular a hydrocarbon-based gas flow, for example originating from a production well.

The pressure reducer 2 makes it possible to reduce the pressure of the gas flow to a value of between 0 and 10 effective bar, preferably between 0 and 5 effective bar, for example approximately 2 effective bar.

It is expedient to purge the device during start-up, by setting the two-way valve 7 to the purge position and opening the control valve 5. Then the control valve 5 is closed, the two-way valve 7 is set to the sampling position, and the control valve 5 is opened to a position making it possible to achieve an appropriate flow rate.

The gas flow rate can be comprised for example between 10 and 100 mL/min. A flow rate of 50 mL/min can be particularly suitable.

The gas flow passes successively, in a continuous flow, through the first gas flow transport line 4, the flow-control valve 5, the second gas flow transport line 6, the two-way valve 7, the third gas flow transport line 9, the contact chamber 10, the fourth gas flow transport line 11, the flow meter 12 and the gas evacuation means 13.

It is wise to keep the gas evacuation means 13 (like the bleed line 8) well away from the operators.

During the passage of the gas flow through the contact chamber 10, the hydrogen sulphide reacts with the solid reagent. Thus, the solid reagent is progressively converted to sulphur-containing solid product, which leads to a change in colouration.

In the case where cadmium acetate crystals are used, the crystals progressively change colour from white to yellow. The change in colouration occurs first for the reagent which is situated on the side of the third gas flow transport line 9 and then spreads to the reagent which is situated on the side of the fourth gas flow transport line 11.

According to a variant, once all of the solid reagent has changed colour, the gas flow supply is cut.

According to another variant, the gas flow supply is cut when a substantial part of the solid reagent has changed colouration (for example at least 50%, or at least 60%, or at least 70%, or at least 80%, or at least 90%) but before all of the solid reagent has changed colouration (i.e. before the change in colouration reaches the distal end of the tube). This variant is advantageous because in this case it is certain that $H_2S$ will not leave the contact chamber, since all of it is consumed as the operation progresses, and is not delivered in excess into the system.

If necessary, the method according to the invention comprises a stage of estimating the change in colouration. For example, this estimation can be carried out by comparing the colour of the material present in the contact chamber (solid reagent or sulphur-containing solid product or mixture of these) with one or more standard colours.

Thus, the change in colouration makes it possible both to qualitatively register the presence of $H_2S$, but also to adjust the sampling of gas to exactly the necessary period, without having to precisely know the $H_2S$ content of the gas, the flow rate in the device or the mass of solid reagent in the contact chamber 10.

In fact, the exact quantity of sulphur sampled by the method according to the invention is not critical from the point of view of an isotopic measurement of the sulphur. The method according to the invention is not primarily intended to quantitatively measure the hydrogen sulphide content of the gas.

The period during which the gas flow is brought into contact with the solid reagent can typically vary from one minute to several days or weeks depending on the $H_2S$ content. A few minutes suffice in the case of a flow of hydrocarbons with a high $H_2S$ concentration, whereas a typical period of 15 days is necessary for a gas with a low $H_2S$ content (for example approximately 2 ppm).

The change in colouration therefore makes it possible to specifically determine the period of exposure necessary in very varied cases. It is also to be noted on this subject that the simplicity and the safety of the system are such that there is no need for an operator to be present alongside the device for the whole of the sampling period. The operator only has to verify at what moment the change in colouration is completed, and then interrupt the circulation of the gas flow by closing the control valve 5.

Once the circulation of the gas flow is interrupted, the operator removes the contact chamber 10 from the device. The contact chamber is plugged (for example by means of silicone plugs) and transported to an installation for the isotopic measurement of the sulphur, which will generally be a specialist laboratory equipped with a mass spectrometer.

The contact chamber is opened on site in a very simple manner, for example by means of a knife or scalpel in the case where the wall 16 of the contact chamber 10 is made of plastic. Alternatively, it is also possible to provide breaking means on the contact chamber itself: for example the contact chamber can be pre-slit so that it can be opened simply by pressing with the fingers.

The sulphur-containing solid product is recovered, and an isotopic measurement of the sulphur is then carried out. The isotopic ratio of the sulphur in the sample and the isotopic deviation is thus measured, i.e. the deviation of this isotopic ratio compared with a standard (generally the isotopic ratio of the sulphates contained in seawater), according to the techniques well known to a person skilled in the art. This measurement provides information on the origin of the hydrogen sulphide content in the initial gas flow, taking account of a set of other parameters (temperature, age of the reservoir of hydrocarbons, type of alteration, composition etc.), as will be assessed by a person skilled in the art.

The method can then be implemented again for a new measurement using the same device, after having cleaned the system by means of for example flushing with inert gas or compressed air (by operating the bleed lines 3, 6), and having placed a new contact chamber in the location provided for this purpose.

Alternatively, if the contact chamber is not detachable, the sulphur-containing solid product is recovered manually after opening the contact chamber.

Then, in order to implement the method again, solid reagent is again inserted manually into the contact chamber, which is then closed again.

EXAMPLE

The following example illustrates the invention without limiting it.

In this example the measurement of isotopic deviation of sulphur 34 ($\delta^{34}S$) is compared by means of the standard method of bubbling through a solution of cadmium acetate and by means of the method described above (solid reagent: cadmium acetate crystals; mass of reagent: approximately 100 mg). The actual isotopic measurements are carried out by means of a mass spectrometer.

The results are given in Table 1 below.

TABLE 1 comparison of the measurement of isotopic deviation of sulphur by conventional sampling or according to the invention

| Origin of the sample | $H_2S$ content of the gas | Measurement of $\delta^{34}S$ by bubbling | Measurement of $\delta^{34}S$ according to the invention |
|---|---|---|---|
| Standard gas (known $H_2S$ content) | 1% | +5.4‰ | +5.3‰ |
| Gas from site No. 1 | 16% | +17.8‰ (measured in 1995) | +19.4‰ |
| Gas from site No. 2 | 7% | −0.14‰ | +2.0‰ |
| Gas from site No. 3 | 2 ppm | −30‰ on average (measurements from 1992 to 2000) | −31.1‰ |

It should be noted that the method according to the invention can be used over a very wide range of $H_2S$ concentrations. Moreover the analytical error produced is less than the natural variability of the isotopic deviation of sulphur.

The invention claimed is:

1. A method for sampling a solid sulphur product comprising:
    supplying a gas flow comprising hydrogen sulphide;
    bringing the gas flow into contact with a solid reagent within a contact chamber and reacting the solid reagent with the hydrogen sulphide contained in the gas flow, said reaction fixing the sulphur of the hydrogen sulphide by forming a sulphur-containing solid product which is different in colour from the solid reagent;
    recovering the sulphur-containing solid product from the contact chamber;
    transporting the sulphur-containing solid product to an installation for the isotopic measurement of the sulphur; and
    isotopically measuring the sulphur of the sulphur-containing solid product within the installation for the isotopic measurement of the sulphur.

2. The method according to claim 1, wherein the solid reagent is constituted by cadmium acetate crystals.

3. The method according to claim 1, wherein the gas flow originates from a deposit of hydrocarbons.

4. The method according to claim 1, wherein the stage of bringing into contact is carried out continuously and the gas flow is evacuated after having been brought into contact with the solid reagent.

5. The method according to claim 1, wherein the pressure in the contact chamber during the stage of bringing into contact is comprised between 0 and 10 effective bar, preferably between 0 and 5 effective bar.

6. The method according to claim 1, implemented by means of a device for sampling a sulphur-containing solid product, said device comprising:
    a contact chamber, comprising a solid reagent, said solid reagent being capable of reacting with hydrogen sulphide and the reaction of the solid reagent with hydrogen sulphide producing a change in colouration and fixing the sulphur of the hydrogen sulphide by forming a sulphur-containing solid product;
    gas flow delivery means, feeding the contact chamber inlet;
    gas flow evacuation means, connected to the contact chamber outlet; and
    means of displaying the change in colouration of the solid reagent in the detachable contact chamber.

* * * * *